US012698465B2

(12) United States Patent
Kugelmeier et al.

(10) Patent No.: US 12,698,465 B2
(45) Date of Patent: Aug. 4, 2026

(54) CELL CULTURE APPARATUS

(71) Applicant: Kugelmeiers AG, Erlenbach (CH)

(72) Inventors: Patrick Kugelmeier, Zollikerberg (CH); Martin Meier, Uster (CH); Guillaume Jung, Wermatswil (CH)

(73) Assignee: Kugelmeiers AG, Erlenbach (CH)

( * ) Notice: Subject to any disclaimer, the term of this patent is extended or adjusted under 35 U.S.C. 154(b) by 809 days.

(21) Appl. No.: 17/926,553

(22) PCT Filed: Mar. 11, 2021

(86) PCT No.: PCT/EP2021/056234
§ 371 (c)(1),
(2) Date: Nov. 18, 2022

(87) PCT Pub. No.: WO2021/233585
PCT Pub. Date: Nov. 25, 2021

(65) Prior Publication Data
US 2023/0193179 A1 Jun. 22, 2023

(30) Foreign Application Priority Data
May 19, 2020 (EP) .................................... 20175312

(51) Int. Cl.
*C12M 1/32* (2006.01)

(52) U.S. Cl.
CPC .................................. *C12M 23/12* (2013.01)

(58) Field of Classification Search
CPC ............................. C12M 23/12; C12M 23/14
See application file for complete search history.

(56) References Cited

U.S. PATENT DOCUMENTS 6,027,695 A 2/2000 Oldenburg
2008/0063572 A1 3/2008 Deutsch et al.
(Continued)

FOREIGN PATENT DOCUMENTS

EP 3150691 A1 * 4/2017 ............ C12M 23/34
WO WO-2008/106771 A1 9/2008
(Continued)

OTHER PUBLICATIONS

Machine Translation of WO 2014/196204 A1 (Year: 2025).*
(Continued)

*Primary Examiner* — Michael L Hobbs
(74) *Attorney, Agent, or Firm* — MARSHALL, GERSTEIN & BORUN LLP

(57) ABSTRACT

The invention relates to a cell culture apparatus for cultivating cell spheroids, comprising at least one compartment having n compartment walls which define a compartment base area and a volume $V_K$ above the compartment base area and a multiplicity of microwells having p top edges and a volume $V_M$, wherein the microwells are arranged in the compartment base area such that the compartment base area outside the microwells merely has inclined surfaces, the number of microwells is chosen such that the entire compartment base area is covered with microwells, all the microwells have the same volume VM and the microwells have the shape of a pyramid or a cone having a rounded tip for accommodation of cells and additionally rounded edges between the tip and the base of the pyramid or the cone.

13 Claims, 11 Drawing Sheets

(56) References Cited

U.S. PATENT DOCUMENTS

2010/0068793 A1* 3/2010 Ungrin ................. C12N 5/0603
435/283.1
2012/0149051 A1* 6/2012 Kugelmeier ........... C12M 23/12
435/325
2016/0032229 A1 2/2016 Egeler
2017/0226455 A1* 8/2017 Fang ...................... C12M 23/12

FOREIGN PATENT DOCUMENTS

WO WO-2010/142755 A2 12/2010
WO WO-2014196204 A1 * 12/2014 ............ C12M 23/08

OTHER PUBLICATIONS

International Search Report for Application No. PCT/EP2021/056234, dated Jun. 17, 2021.
Lehmann R. et al., "Superiority of Small Islets in Human Islet Transplantation" Diabetes. Mar. 2007; 56 (3):594-603.

* cited by examiner

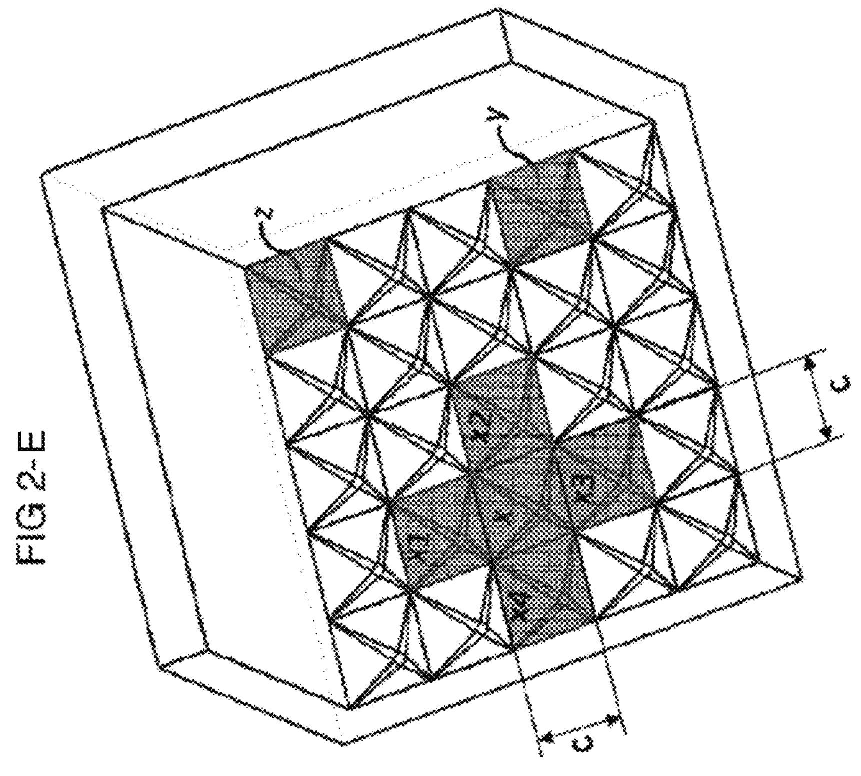
FIG 2-E

CELL CULTURE APPARATUS

CROSS-REFERENCE TO RELATED APPLICATION

This present application is the US national phase of International Patent Application No. PCT/EP2021/056234, filed Mar. 11, 2021, which claims priority to European Application No. 20175312.6, filed Mar. 19, 2020. The priority application, EP 20175312.6, is hereby incorporated by reference in its entirety.

FIELD OF THE INVENTION

The present invention relates to apparatuses for in vitro aggregation of cells. The apparatuses are characterized by containing specially shaped cavities that allow aggregation of individual cells to form cell spheroids when a cell suspension is seeded onto the apparatus. The present invention further relates to a method for aggregation of cells and to the use of the apparatuses according to the invention for aggregation of cells.

BACKGROUND OF THE INVENTION

Stem cell research is concerned with the principles of regeneration processes in tissue in order to develop methods for regenerative medicine. Here, a very important factor of stem cell biology is the constant communication between the stem cells themselves and the interaction of the stem cells and the surrounding tissue, the so-called stem cell niche. Together these cells form organizational units referred to as cell clusters, cell spheroids or “organoids”, which, in large numbers and sophisticated architecture, ultimately form an entire organ.

Various experimental environments allow analysis of such processes, the standard here being the use of “hanging drops”. In this case, the development of stem cells is simulated by placing a certain amount of stem cells and other cells in a drop which then develop to form cell clusters which can be analyzed. The disadvantages of this widely used technology are that in this way only a limited number of cell clusters can be generated and that only limited medium changes can be carried out. This would be important, however, since differentiation of stem cells depends on the presence of certain cytokines at a certain time which could be added upon media exchange.

In the clinical setting, the possibility of large-scale production of cell clusters of a defined size with the possibility of a medium change would be highly desirable for various therapeutic approaches, such as e.g. islet cell transplantation. In this technique, due to limited diffusion-based nutrient and oxygen supply in the early time after transplantation, small islets are better than large islets because large islets die due to lack of oxygen after transplantation. As a result, two to three transplantations are required until enough functional islets are present in the patient to no longer require injected insulin (Lehmann R. et al., Diabetes. 2007 March; 56 (3): 594-603). It would therefore be desirable to produce many small islets instead of fewer large islets. In terms of figures, one transplantation would thus be sufficient to ensure that a diabetic is functionally cured and no longer has to inject insulin. For successful production of small islets and clinical application, islets would have to be dissociated into individual cells and reaggregated to form small “pseudoislets”. For transplantation, about 1,000,000 pseudoislets would be required, a number not achievable with the hanging drop technique.

WO 2008/106771 describes an apparatus for the preparation of cell aggregates. This apparatus is sold under the trade name Aggrewell (Stemcell Technologies, Vancouver, BC, Canada V5Z 1B3). However, this apparatus has only been developed as a laboratory product and not as a medical device, which is why it should only be used for human application with assumption of risk by the user.

In addition, the apparatus described is of limited utility for stem cell cluster production, since the microwells have a purely inverted pyramid shape or the shape of a flat-bottom pyramid. In any case, however, the side edges of the pyramid are not rounded. Thus, instead of being forced into a round spheroid/cluster shape, the cultured cells are forced into a pointed pyramid shape or the corresponding side edges. This is contradictory to the physical basic principles of “free energy minimization”, which all cell processes are subjected to. In addition, in this form of microwells, the cells are not supported in forming a round cell spheroid, but instead forced into an unnatural conformation.

Furthermore, such an apparatus prevents the natural communication mechanisms of cells since different concentrations of oxygen and signal molecules are present for the individual cells in the cell clusters thus formed due to their irregular shape. This apparatus is therefore unsuitable for cell therapies since the shape of the microwells can cause a disruption of the signal paths, which can lead to incorrect programming and ultimately to tumor formation in later applications with stem cells. In addition, this apparatus requires a solution for reducing cell adhesion. This solution is not clinically approved, so that for this reason too the apparatus is not suitable for clinical use.

Only a single apparatus has hitherto been known from the prior art, which enables the growing of cell clusters on the required scale (WO 2010/142755 A2). This apparatus has a multiplicity of microwells with a design. However, it is disadvantageous here that due to technical limitations, the microwells do not cover the entire base area of the apparatus, but a substantially horizontal edge remains along the compartment wall, on which individual cells can potentially deposit. In order to avoid this, WO 2010/142755 A2 proposes the use of inserts which are placed onto the projecting edge.

However, this system entails the risk that, in the event of careless handling, individual cells reach the edge below the edge of the insert, which in the case of stem cells can grow in an uncontrolled manner, which in the worst case can lead to tumor formation in the patient treated with this cell product.

There is therefore a continuing need for cell culture apparatuses which, because of their design, prevent individual cells from settling outside the microwells and from differentiating there in an uncontrolled manner.

Technical Object to be Achieved

The object to be achieved objectively is therefore to provide a cell culture apparatus which is designed such that all introduced cells are cultured under defined conditions and growth of individual cells outside the microwells is prevented.

SUMMARY OF THE INVENTION

The object is achieved by a cell culture apparatus for culturing cell spheroids, comprising

- at least one compartment with n compartment walls and a volume $V_K$ which define a compartment base area, and
- a multiplicity of microwells having p top edges and a volume $V_M$,
- wherein the microwells are arranged in the compartment base area such that the compartment base area outside the microwells has merely inclined surfaces, the number of microwells is chosen such that the entire compartment base area is covered with microwells, all the microwells have the same volume $V_M$, and the microwells have the shape of a pyramid or of a cone having a rounded tip for accommodation of cells, and additionally rounded edges between the tip and the base area of the pyramid or the cone.

The object is further achieved by a method for producing cell spheroids, wherein the cell spheroids are cultured in a cell culture apparatus according to the invention.

DESCRIPTION OF THE INVENTION

Figure 1:
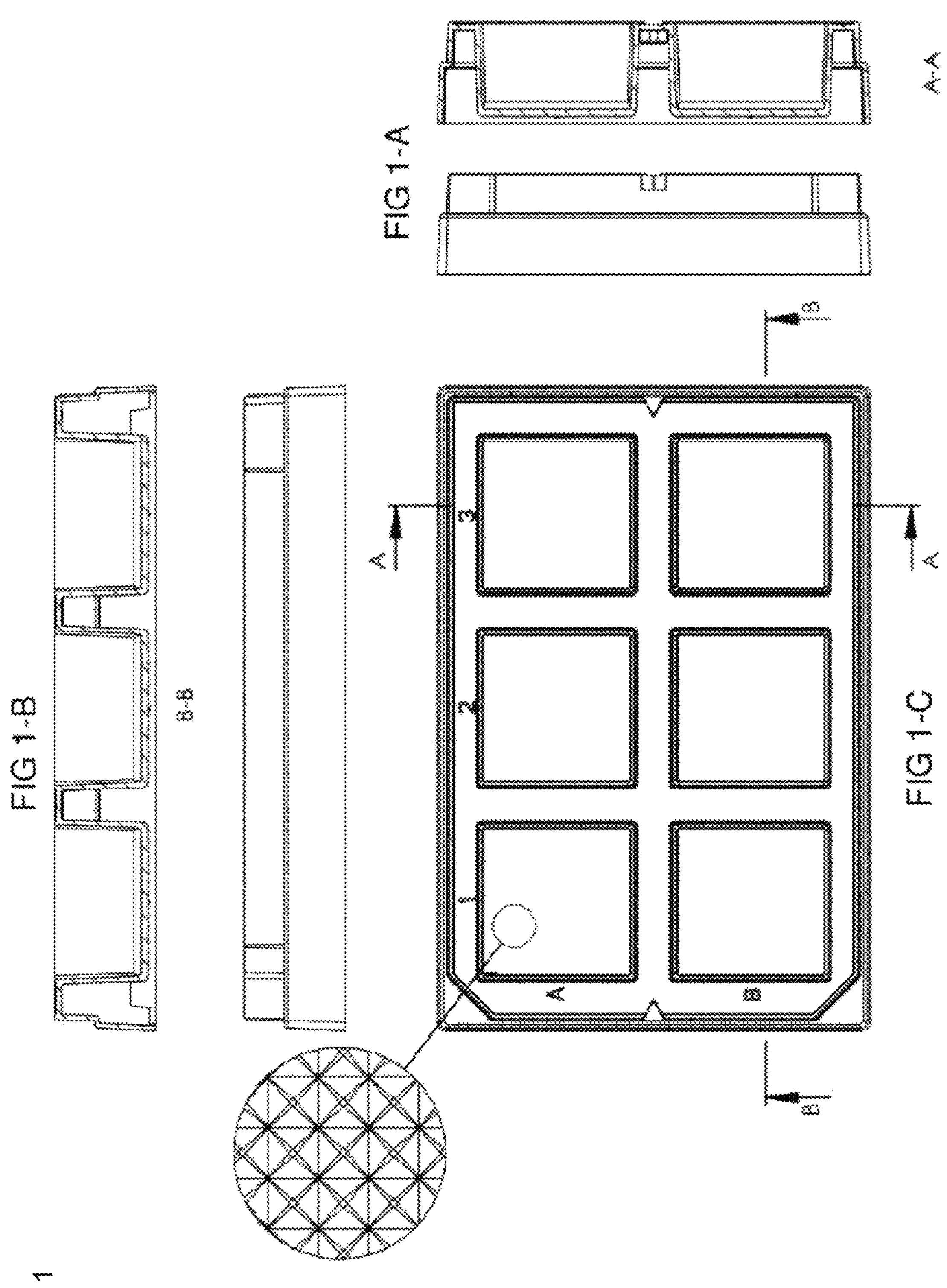
FIG. 1 shows two side views, two sectional views and a top view of a cell culture apparatus according to the invention.

The invention relates to a cell culture apparatus comprising at least one compartment with n compartment walls, which define a compartment base area, and a multiplicity of microwells with p top edges and a volume $V_M$, wherein the microwells are arranged in the compartment base area such that the compartment base area outside the microwells has merely inclined surfaces, the number of microwells is chosen such that the entire compartment base area is covered with microwells, and wherein all microwells have the same volume $V_M$.

According to the present definition, a cell culture apparatus is suitable for culturing eukaryotic cells, in particular stem cells, and differs from assay plates, inter alia, by the material used, surface finish, attachment properties, sterility, gas permeability, light transmission, and refractive index.

In a preferred embodiment, the cell culture apparatus consists of a material that prevents cell adhesion. Such materials comprise, e.g., specifically suitable plastics (e.g. polystyrene, polycarbonate), and glass, with or without coatings to reduce cell adhesion. In a particularly preferred embodiment, the cell culture apparatus consists of cycloolefin copolymers.

The cell culture apparatus according to the invention comprises at least one compartment with n compartment walls. Thus, the cell culture apparatus according to the invention is delimited on all sides by a compartment wall, so that a liquid, e.g., cell culture medium can be held within the compartment. The compartment walls can all have the same or different height. The typical height of a compartment wall is 1 to 100 mm, preferably 10 to 30 mm. In any case, the compartment walls are smooth, i.e. they have no protrusions.

The compartment walls define a compartment base area. This compartment base area extends over the entire area delimited by the compartment walls and is delimited by the compartment walls. In a preferred embodiment, the compartments of the cell culture apparatus according to the invention are open at the top, i.e. the side opposite the compartment base area is not closed, so that the compartments are directly accessible. Compartment volume $V_K$ is above the compartment base area.

The compartments of the cell culture apparatus according to the invention have an n-cornered opening. n can be any natural number. In a preferred embodiment, n is so large that the opening of the compartment is approximately circular. In a further preferred embodiment, n is 3, 4, or 6, particularly preferably 4. Such geometry facilitates production.

In a further embodiment, in each case two compartment walls opposite one another are of equal length, resulting in that the compartment having a symmetrical opening. In a preferred embodiment, all compartment walls are of equal length so that the compartment has an opening in the form of an equilateral triangle, hexagon or, particularly preferably, a square.

In a preferred embodiment, the compartment walls are substantially perpendicular to the compartment base area outside the microwells. Here, each wall angle β of 90° to 110° onto the compartment base area is referred to as substantially perpendicular.

The cell culture apparatus according to the invention comprises at least one compartment, but can also comprise several, e.g. 2, 3, 4, 5, 6, 8, 10, 12, 18, 24, 48, 96, 384, 1536, 3456, or 9600 compartments. Preferably, the cell culture apparatus comprises 4, 6, 12, 24, 96, 384 or 1536 compartments. In a particularly preferred embodiment, the cell culture apparatus comprises 6 compartments.

The cell culture apparatus according to the invention further comprises a multiplicity of microwells having p top edges c. Microwells are defined here as depressions in the compartment base area in which cells settle, approach one another and can grow as cell clusters. Microwells may also be referred to herein as picowells, nanowells, microcavities, and wells.

The microwells of the cell culture apparatus according to the invention have a base area with p corners. In this case, base area G is an opening through which the cells can slide into the interior of the microwells. The opening has p top edges c, which surround the opening. p can be any natural number. In a preferred embodiment, p is so large that the base area G is approximately a circle. In a further preferred embodiment, p is 3, 4, or 6, particularly preferably 4.

In one embodiment, p is n. In a preferred embodiment, p is equal to n and is 4. This ensures optimum utilization of the available base area. In another embodiment, n is 6 and p is 3. In a further embodiment, n is so large that the opening of the compartment is approximately circular and p is 4 or 6. In yet another embodiment, n and p approach infinity.

The microwells have the shape of a pyramid or cone, wherein the tip of the pyramid is located within the compartment base area and the base area of the pyramid or of the cone forms the opening of the microwells. In other words, the volume V of the microwells extends from the surface of the compartment base area into the compartment base area. In the context of the invention, the tip of the pyramid or of the cone is therefore also referred to as the base B of a microwell. Between the tip and the base area G of a microwell, specifically between the corners of the opening and the bottom B, there are the triangular side edges f which delimit the side areas S.

The tips serve to accommodate the cells. The formation of regular spheroids is promoted by the rounding of the tips. In one embodiment, all tips of the microwells of a compartment are equidistant from each other. This is important to maintain communication between spheroids. The cells communicate by means of messenger substances. The transmitted information depends on the concentration of the messenger substances. These principles of morphogen gradients and lateral inhibition require that the distances between the cell spheroids be equal in order for the cell spheroids to develop at the same rate. A safe use in cell therapy is possible only when all cell spheroids are in the same developmental stage during transplantation.

In one embodiment, the microwells have the shape of a pyramid. In a preferred embodiment, the tip of the pyramid is rounded having a diameter $d_B$.

In an embodiment in which p is so large that the base area G is approximately a circle, the microwells have the shape of a cone. In a preferred embodiment, the tip of the cone is rounded having a diameter $d_B$.

In a preferred embodiment, the tip of the cone or of the pyramid has a diameter $d_B$ between 2 μm and 500 μm, preferably 5 μm to 400 μm and particularly preferably 70 μm to 200 μm. In a preferred embodiment, the diameter $d_B$ is 90 μm. In a further preferred embodiment, the diameter $d_B$ 180 μm or 270 μm.

In other words, the tip of the pyramid or of the cone of the microwells has a radius $r_B$ between 1 and 250 μm, preferably 2.5 μm to 200 μm and particularly preferably 35 μm to 100 μm. In a preferred embodiment, the radius $r_B$ is 45 μm. In a further preferred embodiment, the radius $r_B$ is 90 μm or 135 μm.

The microwells have a depth h. The depth is between 10 μm and 2000 μm, preferably 50 μm to 1000 μm, more preferably 100 μm to 500 μm and most preferably 200 μm to 400 μm. In a further preferred embodiment, the depth is 600 μm to 700 μm, particularly preferably 641 μm.

The top edges c have a length between 0 μm to 5 mm, preferably 200 μm to 2 mm, and most preferably 400 μm to 1200 μm. In a preferred embodiment, all top edges are of equal length.

In a preferred embodiment, the triangular side edges f, i.e. the edges between the side areas of the pyramid, are rounded. In a particularly preferred embodiment, the rounding of the triangular side edges f increases progressively from the opening towards the pyramid tip or base of the microwell, wherein s, i.e. the diameter $d_{f1}$ of the rounding close to the opening of the microwells, differs from the diameter $d_{f2}$ close to the tip of the pyramid or the base of the microwells. In a particularly preferred embodiment, $d_{f1}$ is smaller than $d_{f2}$. In a preferred embodiment, $d_{f1}$ is 0 and $d_{f2}$ is $d_B$.

Side areas S form a wall angle α with the base area G or the imaginary area in the opening of the microwells or with the compartment base area. α is between 35° to 75°, preferably 40° to 70°, further preferably 50° to 60° and most preferably 54.7°. This angle ensures that all cells slide down to the bottom or into tip B, and also that optimal conditions exist to assist the cells in forming a natural cell spheroid, but at the same time not constricting them or forcing them into an unnatural conformation.

According to the invention, the depth of the microwells and the length of the top edges depend on radius $r_B$ or diameter $d_B$ and angle α. In a particularly preferred embodiment where a is 54.7°, p is 4 and the diameter $d_B$ is 90 μm, the length of the top edges c is 500 μm, and the depth h is 320 μm. In a further preferred embodiment where a is 54.7°, the diameter $d_B$ is 180 μm, the length of the top edges c is 1000 μm, and the depth h is 641 μm.

Each compartment of the cell culture apparatus according to the invention has a multiplicity of microwells. A multiplicity is defined here as a natural number between 1 and 1,000,000. Accordingly, a compartment comprises between one to 1,000,000 microwells.

In a preferred embodiment, one compartment comprises more than one microwell. In a further preferred embodiment, a compartment comprises exactly one microwell.

According to the invention, the compartment base area of a compartment is completely covered with microwells. The microwells are arranged in such a way that there is as little intermediate space as possible between them. In one embodiment, the microwells are arranged in regular columns and rows. In the context of the invention, there is little interspace between two microwells if the surface of the edge between the two microwells has a width of less than 15 μm.

In one embodiment, each microwell has at least one common top edge with each adjacent microwell.

A common top edge is to be understood here as meaning that the openings of the microwells lie seamlessly next to one another. Thus, in the embodiment in which n equals p and is 4, a microwell x located between four further microwells $x_1$, $x_2$, $x_3$, $x_4$ shares with each of the four adjacent microwells the top edge located between x and $x_1$, $x_2$, $x_3$ and $x_4$, i.e. for $x_1$ it is top edge $c_1$, for $x_2$ it is top edge $c_2$, for $x_3$ it is top edge $c_3$, and for $x_4$ it is top edge $c_4$. A microwell y, which is located in a row or column adjoining a compartment wall, has in each case a common top edge with the three adjacent microwells. A microwell z, which is located in a corner of the compartment base area, has in each case a common top edge with the two adjacent microwells. The same applies to values of n and p not equal to 4.

The common top edge prevents cells from remaining between the microwells, where they could develop in an uncontrolled manner. In the cell culture apparatus according to the invention, all cells are guided into the interior of a microwell due to the particular geometry and arrangement of the microwells, so that each cell can develop correctly in the desired environment.

The top edges of the microwells y and z, which are not shared with the adjacent microwells, are flush with the compartment walls. Flush is defined here as form-fitting, so that at the transition between the top edge and compartment wall no flat edge is created on which individual cells can settle.

In the context of the invention, it is true that a top edge is flush with a compartment wall when the resulting edge has a width of at most 15 μm. In one embodiment, this edge is not horizontal, i.e. parallel to the compartment base area, but inclined.

Because each microwell has at least one common edge with each adjacent microwell, and the top edges of the outer microwells are flush with the compartment walls, the compartment base area outside the microwells has merely inclined surfaces on which no cells can settle. Thus, in the apparatus according to the invention, no cells can grow outside the microwells in an uncontrolled manner.

According to the invention, all microwells have the same volume $V_M$. In other words, in all microwells, the corresponding top edges are each of equal length. In still other words, the cell culture apparatus according to the invention does not have truncated microwells. This ensures that the same growth conditions prevail in all microwells.

According to the invention, all microwells of a compartment are in fluid communication with one another. As a result, the same growth conditions prevail in all microwells.

The invention further relates to the use of the cell culture apparatus described for culturing cells. Due to the special geometry of the microwells, cell clusters can arise from the cultured cells when suitable starting cells and culture conditions are used.

In this case, regularly or irregularly shaped aggregates of cells which extend in all spatial directions are referred to as cell spheroids, cell clusters, organoides or 3D cell colonies. Spherical cell clusters are also referred to as cell spheroids. The terms cell cluster, cell accumulation and cell aggregate are used synonymously herein.

The cell culture apparatuses according to the invention are thus particularly suitable for 3D cell culture with the aim of obtaining cell spheroids. Unlike conventional 3D cultivation methods, no further apparatuses, reactors or special skills of the experimenter are necessary in the cultivation method according to the invention in order to reliably obtain cell spheroids. Instead, the cells may be applied like cells on a conventional cell culture plate, and as a result of the special geometry of the microwells, they automatically form cell steroids which are characterized by a high degree of homogeneity in size and functionality.

This distinguishes the apparatuses according to the invention from previously known apparatuses in which the cells can grow in cell clusters of any shape. This consequently leads to an unequal distribution of oxygen and nutrients within the cell clusters, to the death of individual clusters and thus overall to less functional cell clusters.

A further advantage when using the cell culture apparatus according to the invention is that all cells applied to the cell culture apparatus inevitably grow in cell clusters, since no individual cells remain outside the microwells and can grow there in an uncontrolled manner. This is of enormous importance in particular in therapeutic applications in which the (stem) cell clusters obtained are to be transplanted to a patient. This is also advantageous in research to ensure that only cells with the same properties are present.

Basically, all types of cells can be cultured in the cell culture apparatus according to the invention. However, culturing eukaryotic cells is particularly preferred. Any animal cells can be cultured with the cell culture apparatus according to the invention, in particular mammalian cells, particularly preferably human cells.

In a preferred embodiment, the cell culture apparatus is used to culture stem cells. Through the use of the cell culture apparatus according to the invention stem cell spheroids suitable for use in regenerative medicine can be obtained from stem cells. Such stem cell spheroids have already been successfully used experimentally for the regeneration of various organs and tissues, including heart, lungs, liver, salivary glands, bone tissue, skin, thymus and nerve cells (Ong CS, Zhou X, Han J, et al. In vivo therapeutic applications of cell spheroids. Biotechnology Advances. 2018 March-April; 36(2): 494-505.). Transplantation of such stem cell spheroids, however, entails the risk of tumor formation when the cell spheroids are wrongly programmed. The geometry of the microwells and the arrangement in the apparatus according to the invention can prevent incorrect programming of the stem cells so that stem cells spheroids thus obtained are safe for therapeutic use.

In another preferred embodiment, the cell culture apparatus is used to culture islet cells. The term "islet cells" is familiar to the person skilled in the art and relates to a group of insulin-producing cells from the human pancreas. Diabetes can be cured functionally by transplantation of these cells. Islet cell spheroids known from the prior art are usually too large, which is why they most of them die during transplantation due to lack of oxygen. By using the cell culture apparatus according to the invention, the size of the spheroids can be standardized and thus their survival rate can be improved, since, with an optimum size, oxygen can diffuse to the center.

In a further preferred embodiment, the cell culture apparatus is used to culture tumor cells. According to current medical knowledge tumor cells are degenerate stem cells (so-called "cancer stem cells"). The cell culture apparatus according to the invention can therefore also be used for obtaining tumor cell spheroids. Thus, e.g., tumor cells isolated from patients can be cultured as spheroids that exhibit exactly the same characteristics as the patient's tumor. Thus, therapies can be tested outside of the body (ex vivo), e.g., which chemotherapy is to be used precisely in the patient. These tumor cell spheroids also offer a great potential for drug development and can thus also reduce the number of animal experiments required.

The invention further relates to cell spheroids which can be obtained when using the cell culture apparatus described. These cell spheroids can be used for medical applications, e.g., as a drug. Accordingly, the invention also relates to methods of treating the human body in which cell spheroids cultured by means of the apparatuses of the invention are administered. The range of application is enormous and comprises practically all organ systems, e.g., the treatment of myocardial infarction, cardiac weakness, liver failure, stroke, wound healing, pulmonary fibrosis or vascular disorders.

Preferred embodiments of the present invention are described below with reference to the figures.

Figure 2:
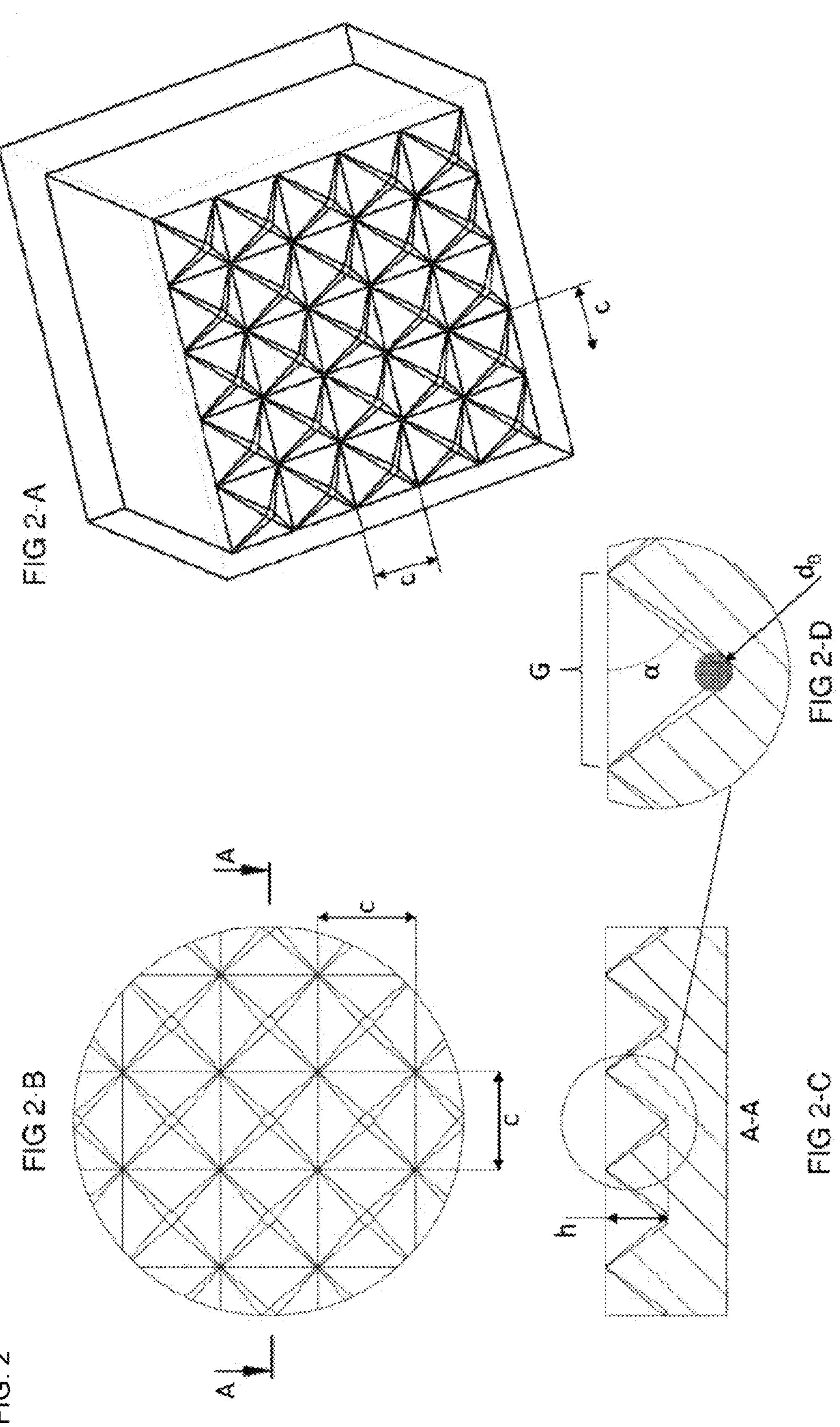
FIG. 2 shows an isometric view, a top view as well as a sectional view as well as two detail views of the arrangement of the microwells in an embodiment of the apparatus according to the invention. Here, h denotes the depth of the microwells, c denotes the top edges of the base area G, a denotes the angle between the side areas S with the base area G, and d denotes the diameter of the rounded tip.

In the embodiment shown in FIGS. 1 and 2, the cell culture apparatus has six compartments wherein n is 4. Here, the microwells have p which is 4. The microwells are arranged such that each microwell has a common top edge with each adjacent microwell (cf. FIG. 3A). In addition, the microwells have the same volume V and a rounded tip with a diameter $d_B$ or radius $r_B$. G denotes the imaginary base area of the pyramid, c denotes the top edges which delimit the base area. The side areas of the microwells form an angle α with the base area.

Figure 3:
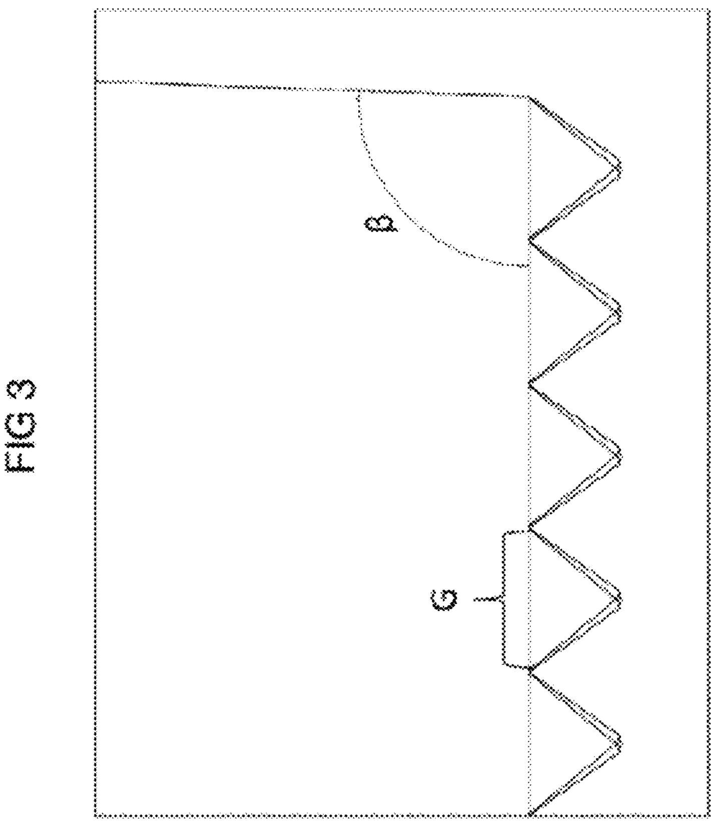
FIG. 3 shows a sectional view of part of an apparatus according to the invention. G denotes the base area of a microwell, β denotes the angle between the compartment wall and the compartment base area.

FIG. 3 shows a sectional view of an apparatus according to the invention at the transition between compartment base area and compartment side wall. Between compartment base area and compartment side wall there is angle α which is approximately 90° C. There is no edge between the compartment side wall and the adjacent microwell.

Figure 4:
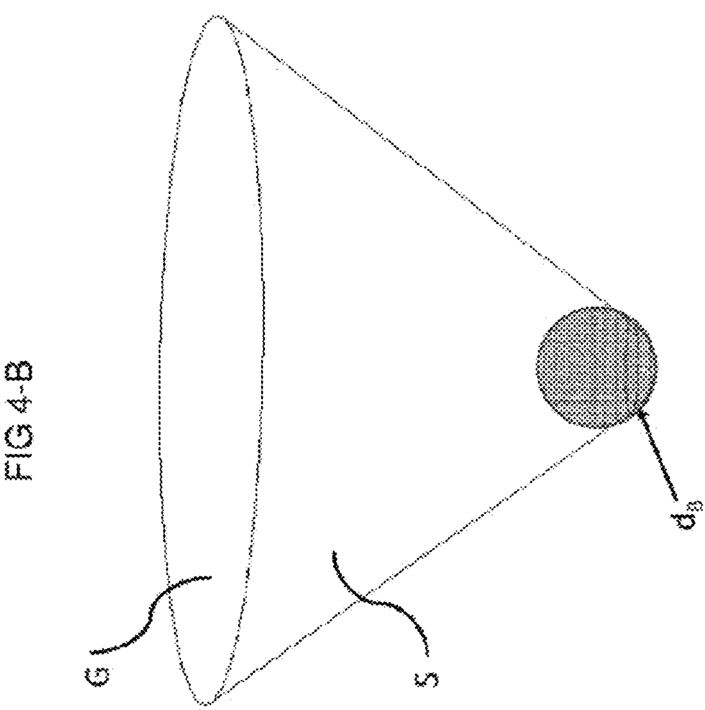
FIG. 4 shows an isometric view of a pyramidal microwell having a rounded tip according to an embodiment of the apparatus according to the invention. In this case, G denotes the base area of the microwell, S denotes the side area of the microwell, c denotes the top edges of the base area G, f denotes the side area edges, d denotes the diameter of the rounded tip, $d_{f1}$ denotes the diameter of the rounding of the side area edge close to base area G, and $d_{f2}$ denotes the diameter of the rounding of the side area edge close to the tip of the pyramid.
Figure 4:
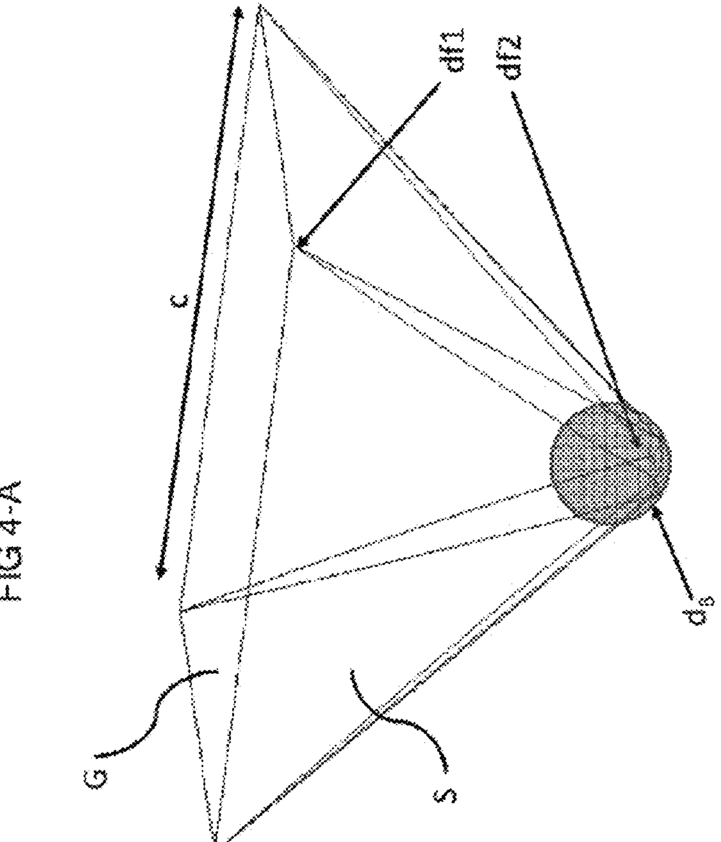

FIG. 4 shows an embodiment of a single microwell in which the microwell is in the form of a pyramid (FIG. 4A) or cone (FIG. 4B) having a rounded tip. The pyramid has rounded edges f between the side areas S, the diameter $d_{f1}$ of the rounding close to the opening or base area G being smaller than the diameter $d_{f2}$ close to the pyramid tip. It can be seen that $d_{f2}$ corresponds approximately to $d_B$.

Figure 5:
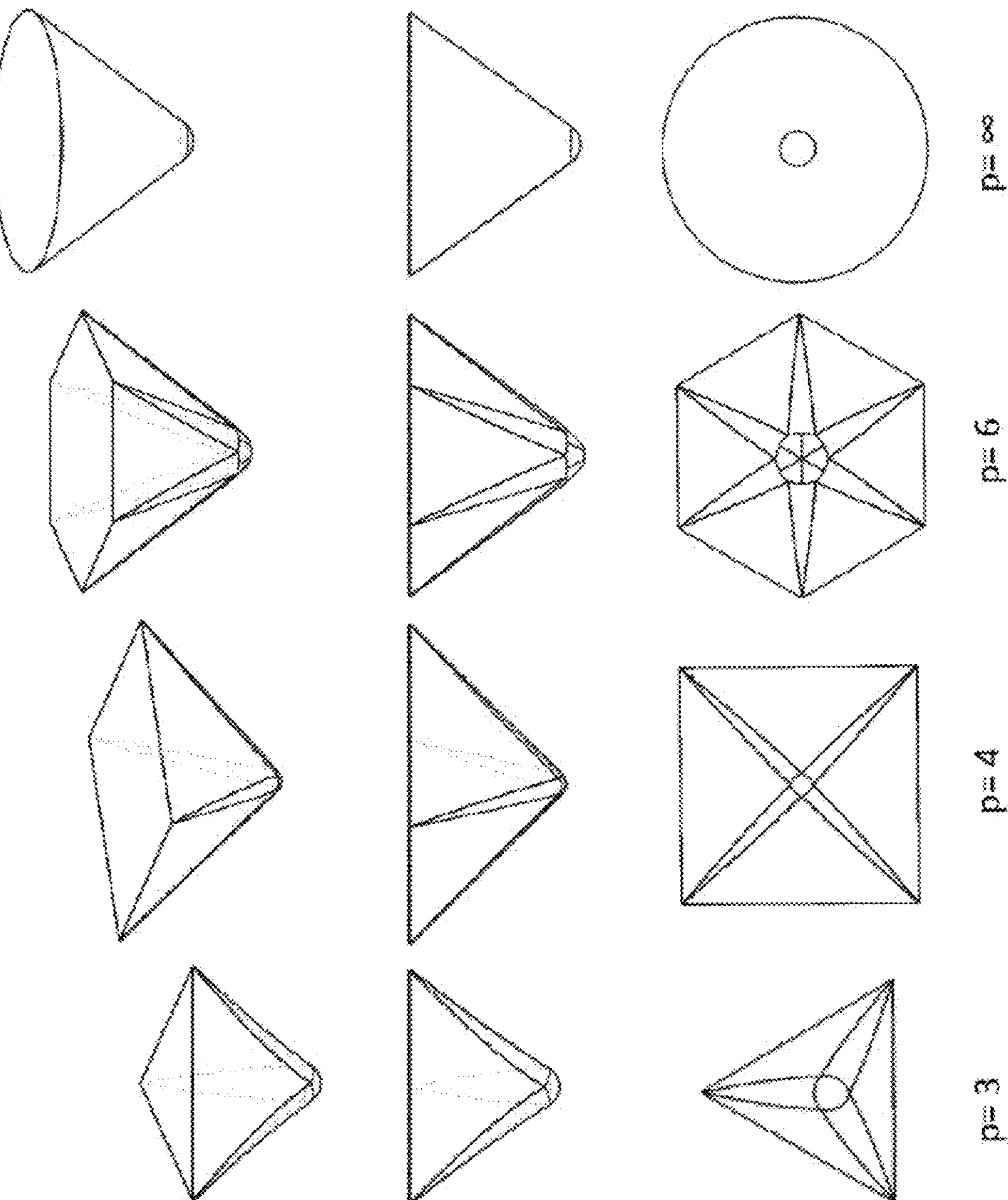
FIG. 5 shows a top view, isometric view and side view of microwells of an apparatus according to the invention with p equal to 3, 4, 6 or infinitely large.

FIG. 5 shows various embodiments of the microwells according to the invention. For example, p is 3 and the microwell has the shape of a trilateral pyramid having a rounded tip. In another embodiment, p is 4 and the microwell has the shape of a quadrilateral pyramid having a rounded tip. In another embodiment, p is 6 and the microwell has the shape of a hexalateral pyramid having a rounded tip. In another embodiment, p is so large that the base area G of the microwell is approximately circular and the microwell has the shape of a cone having a rounded tip. As can be seen from FIG. 5, in all these embodiments the triangular side edges f are rounded, the diameter of the rounding $d_{f1}$ close to the opening or the base area G being smaller than the diameter $d_{f2}$ close to the pyramid or cone tip.

Figure 6:
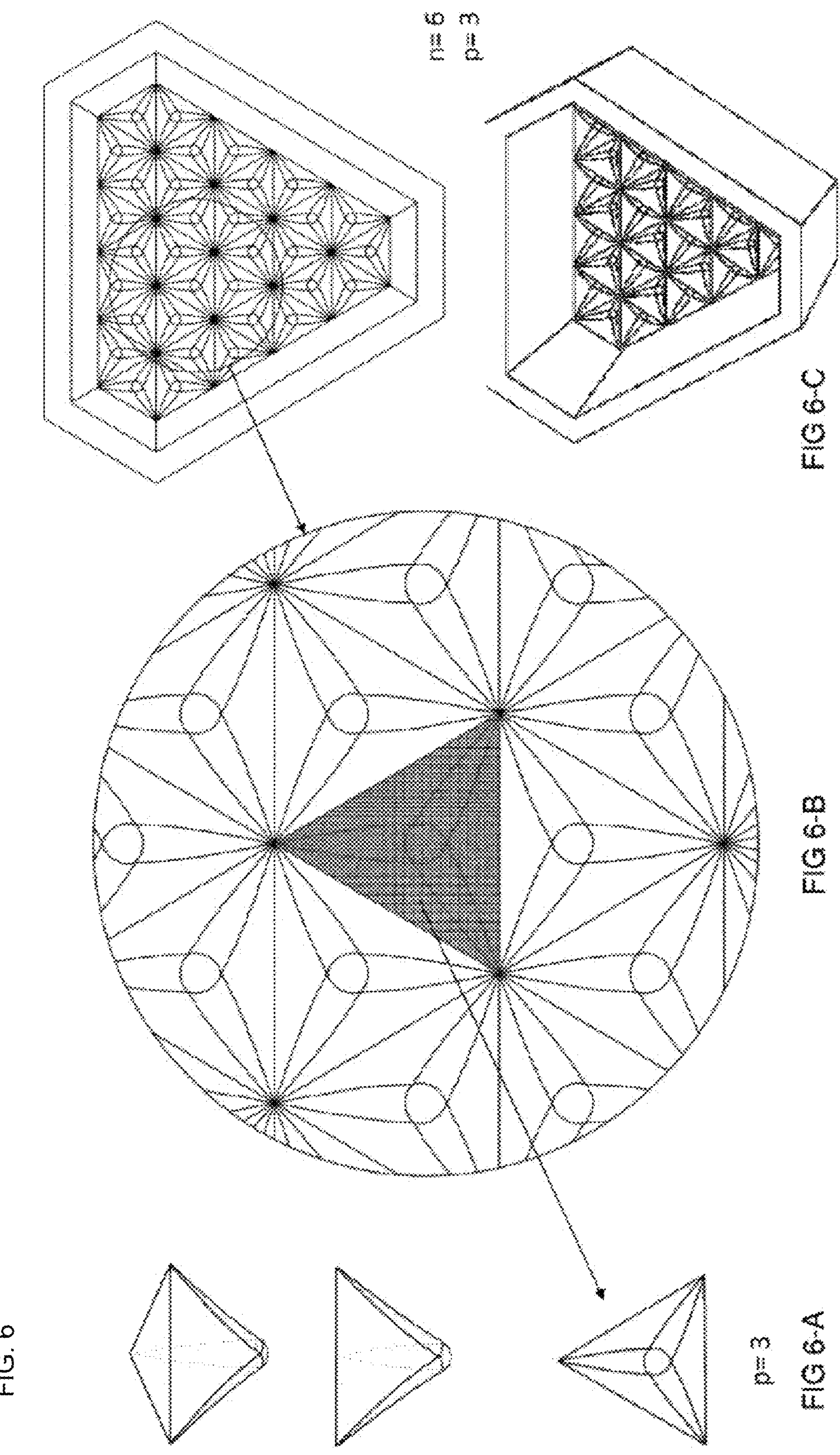
FIG. 6 shows a top view of an arrangement of microwells according to the present invention, and a top view, sectional view and isometric view of a microwell, wherein p is 3 and n is 6.

FIG. 6 shows an apparatus according to the invention with p=3 and n=6. In this case, the microwells have the shape of a trilateral pyramid having a rounded tip and rounded edges between the side areas (cf. FIG. 6A).

Figure 7:
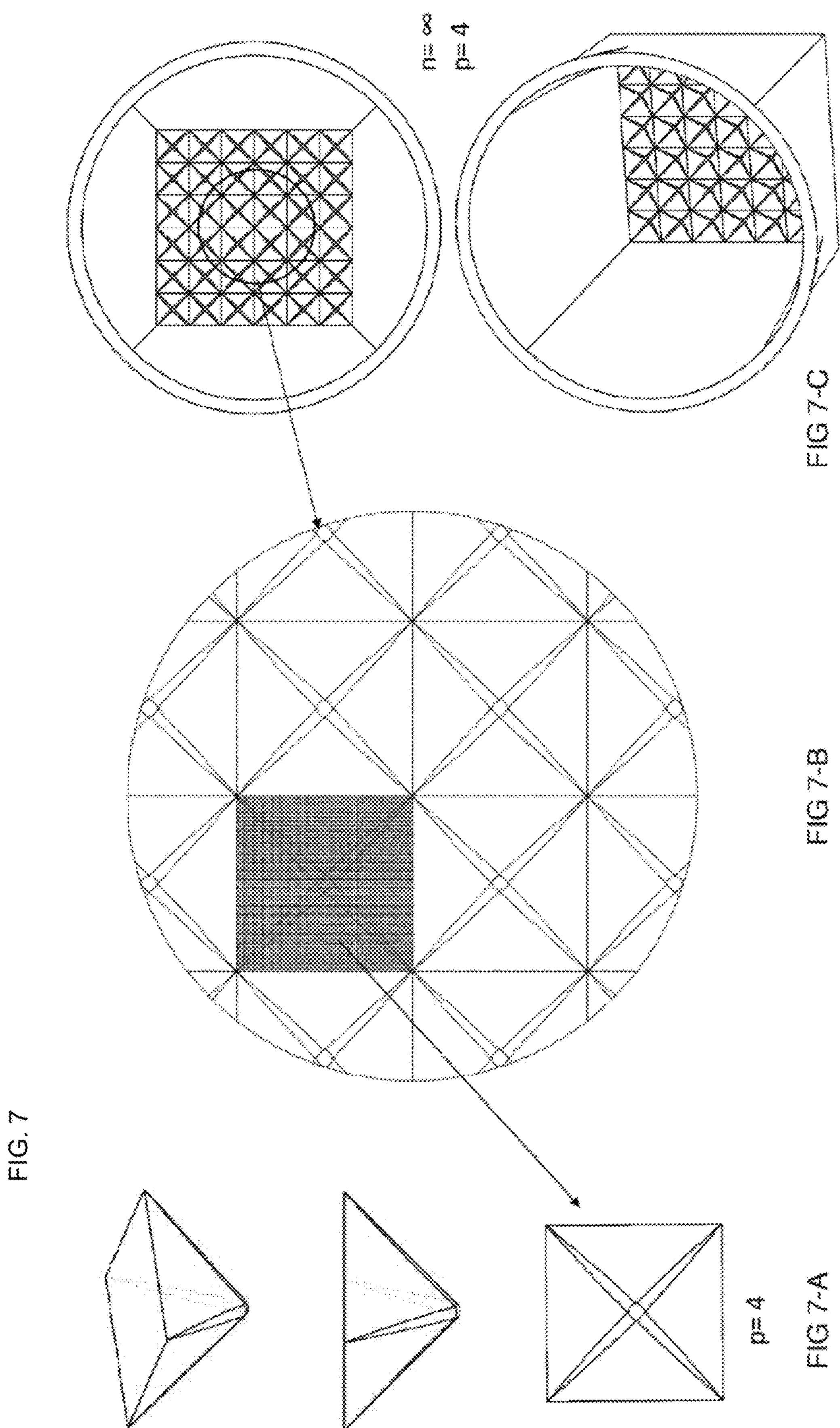
FIG. 7 shows a top view of an arrangement of microwells according to the present invention, and a top view, sectional view and isometric view of a microwell, wherein p is 4.

FIG. 7 shows an apparatus according to the invention with p=4 and n=∞. In this case, the microwells have the shape of a quadrilateral pyramid having a rounded tip and rounded edges between the side areas (cf. FIG. 7A).

Figure 8:
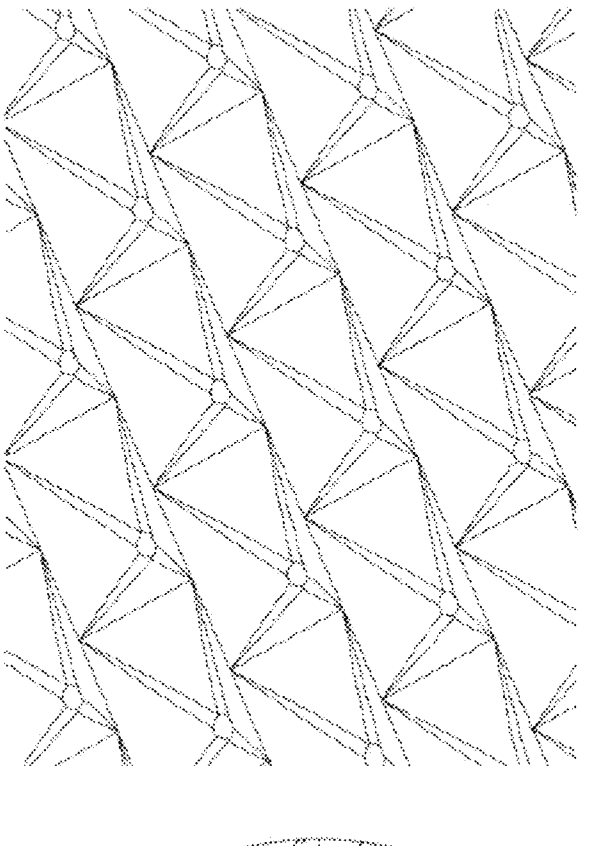
FIG. 8 shows a top view and isometric view of an arrangement of microwells according to the present invention as well as a top view, sectional view and isometric view of a microwell, wherein p is 4.
Figure 8:
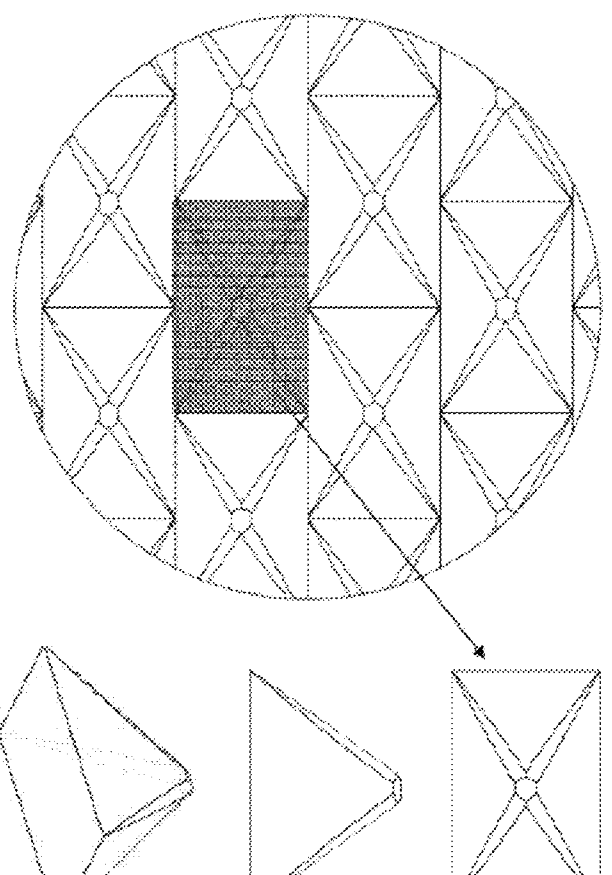

FIG. 8 shows a further arrangement of microwells with p=4 in an apparatus according to the invention. In this case, the microwells have the shape of a quadrilateral pyramid having a rounded tip and rounded edges between the side areas (cf. FIG. 8A).

Figure 9:
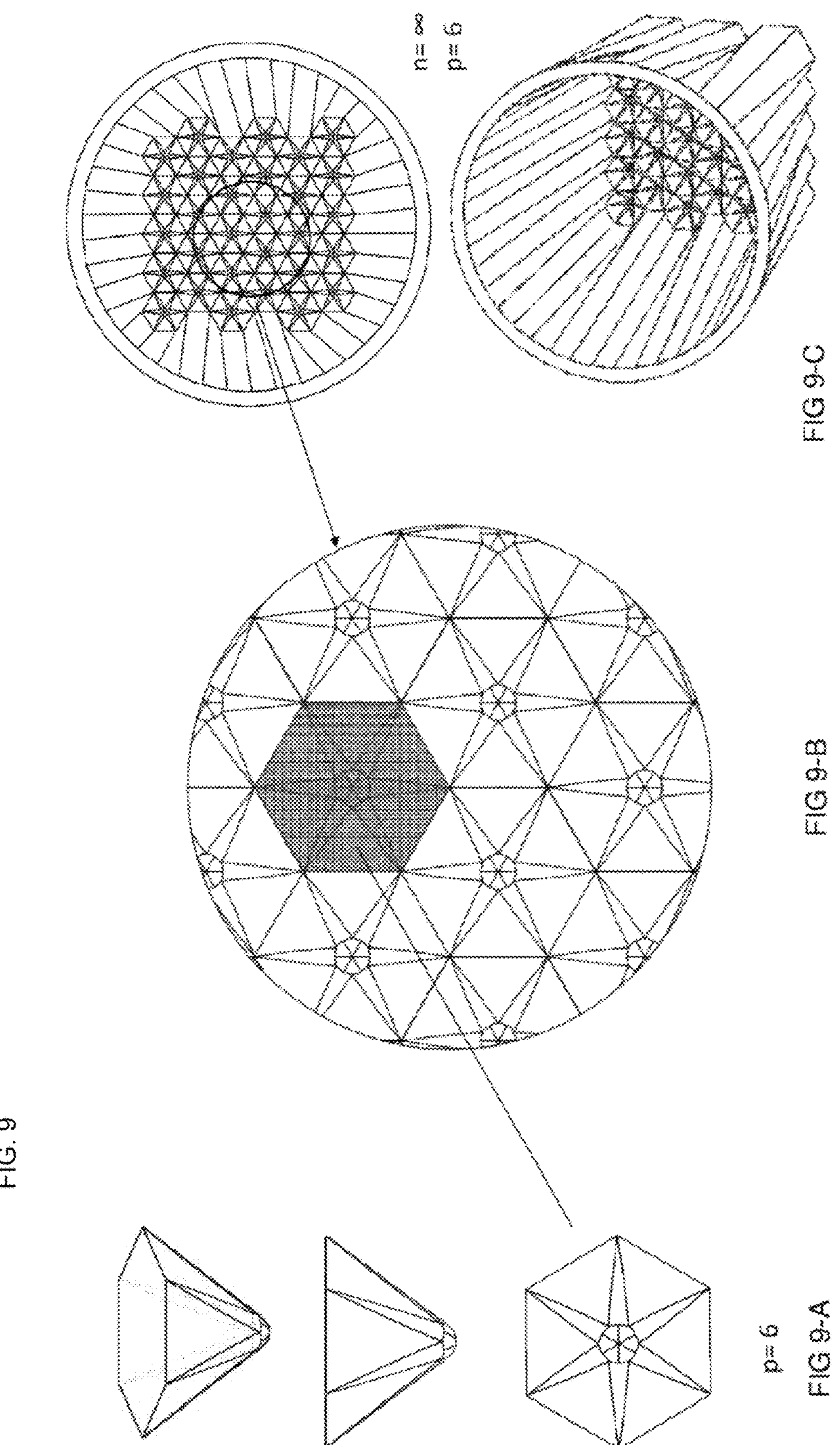
FIG. 9 shows a top view of an arrangement of microwells according to the present invention, as well as a top view, sectional view and isometric view of a microwell, wherein p is 6 and n approaches infinity.

FIG. 9 shows an apparatus according to the invention with p=6 and n=∞. In this case, the microwells have the shape of a hexalateral pyramid having a rounded tip and rounded edges between the side areas (cf. FIG. 9A).

Figure 10:
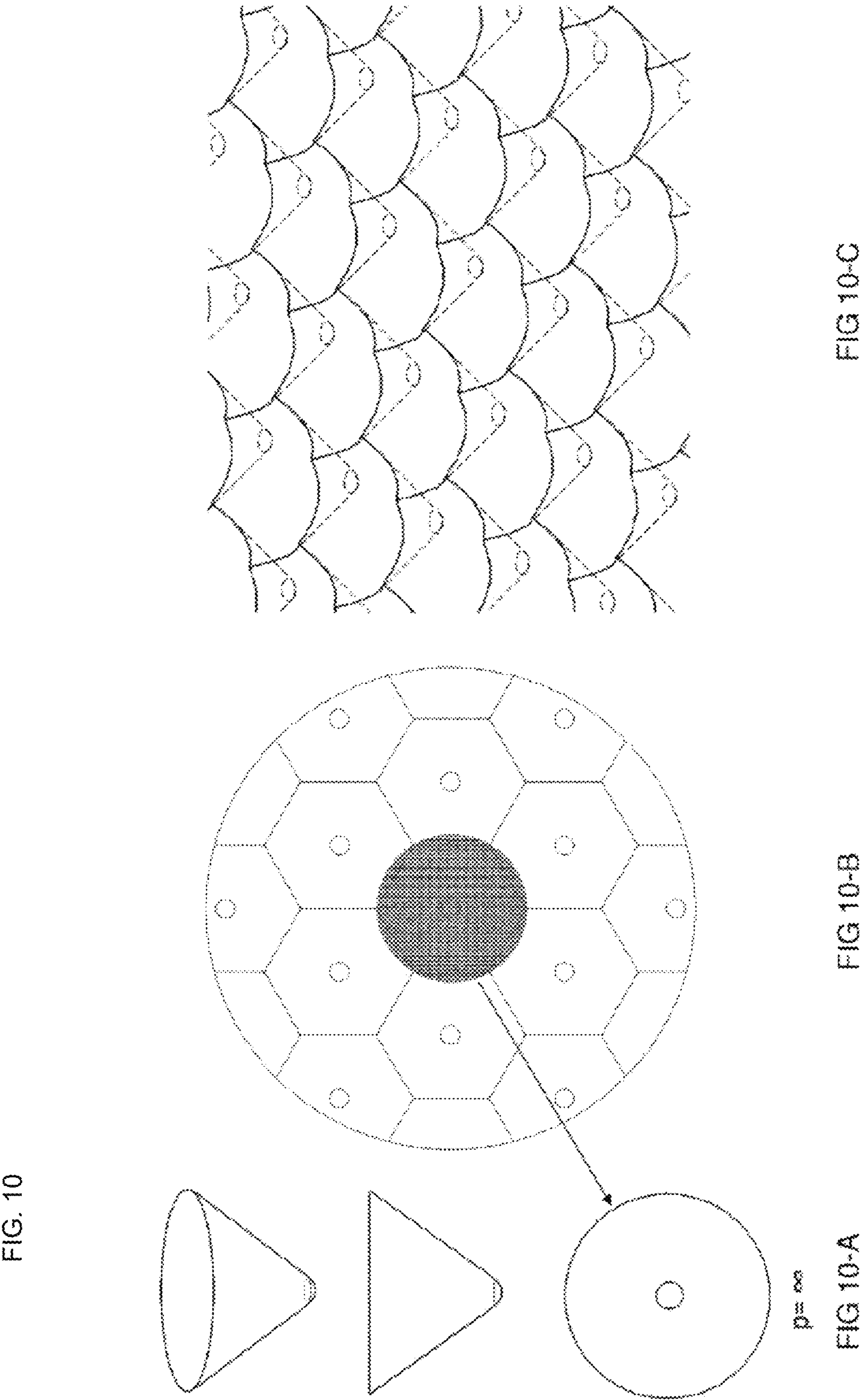
FIG. 10 shows a top view and isometric view of an arrangement of microwells according to the present invention, as well as a top view, sectional view and isometric view of a microwell, wherein p approaches infinity.

FIG. 10 shows an arrangement of microwells in an apparatus according to the invention with p=∞. The microwells have the shape of a cone having a rounded tip (cf. FIG. 10A). Here too, the microwells have a common top edge with each adjacent microwell.

The invention claimed is:

1. A cell culture apparatus for culturing cell spheroids, comprising at least one compartment with n compartment walls which define a compartment base area, and a volume ($V_K$) above the compartment base area, where n is at least 3 and a multiplicity of microwells having p top edges, where p is at least 3, and a volume ($V_M$), wherein each compartment wall is arranged flush with at least one top edge of at least one microwell, and wherein the microwells are arranged in the compartment base area such that each microwell has a common top edge with each adjacent microwell, the number of microwells is chosen such that the entire compartment base area is covered with microwells, all the microwells have the same volume ($V_M$), and the microwells have the shape of a pyramid or of a cone having a rounded tip for accommodation of cells, and additionally rounded edges between the tip and the base area of the pyramid or the cone.

2. The cell culture apparatus according to claim 1, wherein all the tips of the microwells of a compartment are equidistant from each other.

3. The cell culture apparatus according to claim 1, wherein the microwells have side surfaces and the side surfaces form an angle of 54.7° with the compartment base area.

4. The cell culture apparatus according to claim 1, wherein two opposing compartment walls are of equal length.

5. The cell culture apparatus according to claim 1, wherein all top edges of the microwells are of equal length.

6. The cell culture apparatus according to claim 1, wherein n and/or p are/is one of 3, 4, or 6.

7. The cell culture apparatus according to claim 1, wherein n and/or p are so large that the compartment and/or the microwells have an approximately round base area.

8. The cell culture apparatus according to claim 1, wherein n is equal to p.

9. The cell culture apparatus according to claim 1, comprising 1, 2, 4, 6, 12, 24, 96, 384, 1536, 3456 or 9600 compartments.

10. A method for producing cell spheroids, wherein the cell spheroids are cultured in a cell culture apparatus according to claim 1.

11. A use of a cell culture apparatus according to claim 1 for culturing stem cell spheroids.

12. A plurality of cell spheroids obtained by culturing cells in a cell culture apparatus according to claim 1.

13. The cell spheroids according to claim 12, wherein the cells are one of islet cells, stem cells, or tumor cells.

* * * * *